US009962125B2

(12) United States Patent
Hwang

(10) Patent No.: US 9,962,125 B2
(45) Date of Patent: May 8, 2018

(54) METHOD OF COMPRESSING IMAGE IN DIGITAL PATHOLOGY SYSTEM

(71) Applicant: Infinitt Healthcare Co., Ltd., Seoul (KR)

(72) Inventor: Man Won Hwang, Incheon (KR)

(*) Notice: Subject to any disclaimer, the term of this patent is extended or adjusted under 35 U.S.C. 154(b) by 137 days.

(21) Appl. No.: 15/217,167

(22) Filed: Jul. 22, 2016

(65) Prior Publication Data

US 2018/0008202 A1    Jan. 11, 2018

(30) Foreign Application Priority Data

Jul. 11, 2016  (KR) .................. 10-2016-0087657

(51) Int. Cl.
| | |
|---|---|
| *G06K 9/00* | (2006.01) |
| *A61B 5/00* | (2006.01) |
| *H04N 19/176* | (2014.01) |
| *G06K 9/46* | (2006.01) |
| *G06T 7/00* | (2017.01) |

(52) U.S. Cl.
CPC .......... *A61B 5/7232* (2013.01); *A61B 5/725* (2013.01); *G06K 9/4604* (2013.01); *G06T 7/0012* (2013.01); *H04N 19/176* (2014.11); *G06T 2207/20144* (2013.01)

(58) Field of Classification Search
None
See application file for complete search history.

(56) References Cited

U.S. PATENT DOCUMENTS

2003/0227673 A1* 12/2003 Nakagawa .......... G02B 21/241
                                                         359/380
2014/0293117 A1* 10/2014 Murakami .......... G02B 21/365
                                                         348/349

FOREIGN PATENT DOCUMENTS

KR    10-1559798    10/2015

OTHER PUBLICATIONS

English translation of 10-1559798.

* cited by examiner

*Primary Examiner* — Shervin Nakhjavan
(74) *Attorney, Agent, or Firm* — Antonio Ha & U.S. Patent, LLC

(57) ABSTRACT

Disclosed is an image compression method of a digital pathology system. The image compression method is a method of compressing digital slide images having first to nth original plane images (n is a natural number greater than or equal to 2). The image compression method includes selecting a block having an optimal focal point as an optimal block from each set of blocks positioned at identical positions of the first to nth original plane images; forming one plane image as a virtual optimal plane image by combining only the optimal blocks; generating block descriptors for forming the first to nth original plane images based on the virtual optimal plane image; generating first to nth predictive plane images from the virtual optimal plane image such that the first to nth predictive plane images are the least out of focus by using location information for the blocks and the block descriptors; generating first to nth differential plane images, the first differential plane image corresponding to a difference between the first original plane image and the first predictive plane image and the nth differential plane image corresponding to a difference between the nth original plane image and the nth predictive plane image; and compressing the first to nth differential plane images.

7 Claims, 4 Drawing Sheets

Optimal focal point section in edge section of sample

Optimal focal point section for each sample plane

METHOD OF COMPRESSING IMAGE IN DIGITAL PATHOLOGY SYSTEM

CROSS-REFERENCE TO RELATED APPLICATION

This application claims priority to and the benefit of Korean Patent Application No. 2016-0087657, filed on Jul. 11, 2016, the disclosure of which is incorporated herein by reference in its entirety.

BACKGROUND

1. Field

The present invention relates to a method of compressing an image in a digital pathology system, and more particularly, to a digital pathology system that employs an optimal compression method that can effectively remove redundancy to dramatically decrease the size of a multi-plane image that had to be excessively large by using a compression algorithm according to the present invention.

2. Discussion of Related Art

Pathology is a basic medical science for studying a state of a disease or a change in a tissue structure, an organic form, or an organic function of a pathogen in order to find a cause of the disease.

In particular, digital pathology is an image-based information environment which is enabled by computer technology that allows for the management of information generated from a digital slide. Digital pathology is enabled in part by virtual microscopy, which is the practice of producing an image with a microscope and delivering the produced image to a computer network.

Digital pathology is globally recognized as an emerging field of diagnostic medicine. This is because, compared to a well-known and existing method, digital pathology may achieve even better, faster and cheaper diagnosis, prognosis and prediction of cancer which is the biggest enemy of modern people's health or other important diseases.

As in the above, digital pathology is getting the spotlight as an emerging field of diagnostic medicine. However, the research and development is still in an early stage. The current stage of the research and development can be guessed from the following circumstance. In Korea, there is little research and development on a digital pathology system, and also there is no product associated with the research and development. Even in foreign countries, there is no digital pathology system that is approved for primary diagnosis by the U.S. Food and Drug Administration (FDA).

While generating and storing digital slide images (Whole-Slide Image; WSI), when a sample does not have a uniform thickness for each part, such a digital pathology system performs scanning and storage operations by adjusting a focal point instead of applying a single focal point. For an image that has various z-planes having different focal points, the amount of data increases in proportion to the number of planes. For a digital slide image, since even a single-plane image is extremely large, much time and cost are required to store and send the image. Furthermore, since a multi-plane image is several times greater in size than the single-plane image, too much time and cost are consumed to store and send the image. These are considered as obstacles for digitalizing pathology data.

Examining related patent documents, Korean Patent No. 10-1559798, which was registered on Oct. 6, 2015, discloses a method for normalizing an image in digital pathology. In detail, the above patent document discloses the steps of choosing a sample for image normalization, analyzing a spectrum of a certain part of the chosen sample to collect information about a material included in the certain part of the sample, finding a correlation equation through the collected information, correcting the entire image of the sample using the correlation equation, and normalizing the image of the sample through the corrected image.

However, the related patent document does not offer an opinion on the problems caused when the multi-plane image is used as described above.

SUMMARY

The present invention provides a digital pathology system that employs an optimal compression method that can effectively remove redundancy to dramatically decrease the size of an image.

According to an aspect of the present disclosure, there is provided an image compression method for a digital pathology system. The image compression method is a method of compressing digital slide images having first to nth original plane images (n is a natural number greater than or equal to 2). The image compression method includes selecting a block having an optimal focal point as an optimal block from among blocks positioned at identical positions of the first to nth original plane images; forming one plane image as a virtual optimal plane image by combining only the optimal blocks; generating block descriptors for forming the first to nth original plane images based on the virtual optimal plane image; generating first to nth predictive plane images from the virtual optimal plane image such that the first to nth predictive plane images are the least out of focus by using location information for the blocks and the block descriptors; generating first to nth differential plane images, the first differential plane image corresponding to a difference between the first original plane image and the nth differential plane image corresponding to a difference between the nth original plane image and the nth predictive plane image; and compressing the first to nth differential plane images.

Each of the descriptors may include an estimated kernel for performing conversion into an original image of a corresponding plane block based on location information for the block and a corresponding block of the virtual optimal plane image.

The optimal block selection step may include: analyzing each of the blocks positioned at identical positions of the first to nth original plane images to extract a foreground; calculating a blur for the extracted foreground; calculating brightness distortion for the extracted foreground; calculating contrast distortion for the extracted foreground; evaluating quality of an image of the corresponding block using the blur, the brightness distortion, and the contrast distortion by the image quality evaluation unit.

The calculating of a blur may include finding a set E including all edge pixels in the foreground using a sobel filter; and calculating the blur using Equation 1 below:

$$\text{Blur} = \frac{\sum_{I(x,y) \in E} \sqrt{\sum_{I(x',y') \in N_{xy}} \{I(x,y) - I(x',y')\}^2 / |N_{xy}|}}{\sum_{I(x,y) \in E} I(x,y)}, \quad \text{[Equation 1]}$$

where $N_{xy}$ is a set of 8 pixels adjacent to a pixel I(x, y), I(x, y)∈E, and an absolute value of $N_{xy}$ is the total number of pixels in the set $N_{xy}$.

The calculating of brightness distortion may include determining that a pixel in the foreground has a brightness of 0 when the pixel is absolute black and determining that the pixel has a brightness of 1 when the pixel is absolute white; and calculating the brightness distortion by averaging brightness values of all pixels in the foreground.

The calculating of contrast distortion may include: converting the foreground into gray; calculating a cumulative histogram; and calculating the contrast distortion using Equation 2 below:

Contrast distortion=(histogram binary corresponding to 75% of the maximum value of the cumulative histogram−histogram binary corresponding to 25% of the maximum value)/(maximum in range of pixel value−minimum in range of pixel value). [Equation 2]

The quality (IQ) of the block may be defined using Equation 3 below:

$$IQ=1-(ax+by+cz),$$ [Equation 3]

where a+b+c=1, x indicates a blur, y indicates brightness distortion, and z indicates contrast distortion.

BRIEF DESCRIPTION OF THE DRAWINGS

The above and other objects, features and advantages of the present disclosure will become more apparent to those of ordinary skill in the art by describing in detail exemplary embodiments thereof with reference to the accompanying drawings, in which.

DETAILED DESCRIPTION OF EXEMPLARY EMBODIMENTS

Figure 1:
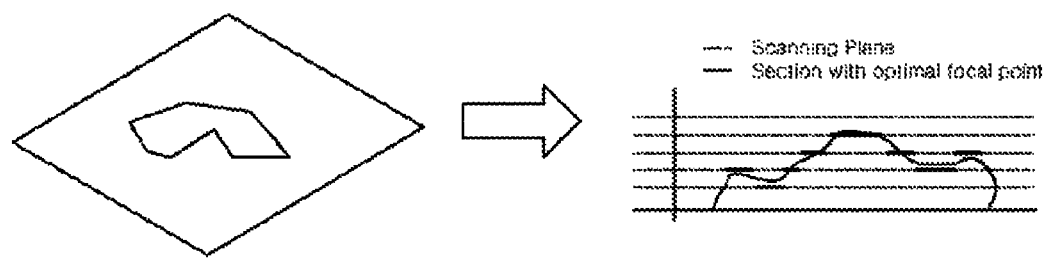
FIG. 1 is a view for describing why a plurality of different focal points are formed in a sample in an image compression method for a digital pathology system according to the present invention.
Figure 1:
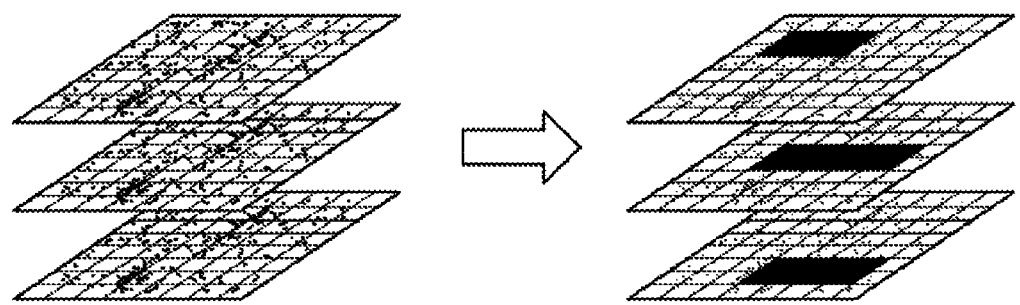

Hereinafter, preferred embodiments of the present invention will be described below in more detail with reference to the accompanying drawings. Terms and words used in the specification and the claims shall not be interpreted as commonly-used dictionary meanings, but shall be interpreted as to be relevant to the technical scope of the invention based on the fact that the inventor may properly define the concept of the terms to explain the invention in best ways.

Therefore, the embodiments and the configurations depicted in the drawings are for illustrative purposes only and are not intended to represent all technical scope of the embodiments, so it should be understood that various equivalents and modifications may exist at the time of filing this application.

As described above, the digital pathology system is applied to an image-based environment that is capable of acquiring, managing, and interpreting pathology information generated from digitized glass slides.

FIG. 1 is a view for describing why a plurality of different focal points are formed in a sample in an image compression method for a digital pathology system according to the present invention. Viewing a side edge of the sample as shown in FIG. 1, there are a plurality of sections in which focal points are different. Accordingly, in order to acquire a plane image having an optimal focal point on a sample plane, a plurality of images need to be acquired on the basis of the focal points.

An image compression method for a digital pathology system according to the present invention is a method of compressing digital slide images having first to nth original plane images (n is a natural number greater than or equal to 2). The image compression method includes selecting a block having an optimal focal point as an optimal block from each set of blocks positioned at identical positions of the first to nth original plane images; forming one plane image as a virtual optimal plane image by combining only the optimal blocks; generating block descriptors for forming the first to nth original plane images based on the virtual optimal plane image; generating first to nth predictive plane images from the virtual optimal plane image by using the block descriptors; generating first to nth differential plane images, the first differential plane image corresponding to a difference between the first original plane image and the first predictive plane image and the nth differential plane image corresponding to a difference between the nth original plane image and the nth predictive plane image; and compressing the first to nth differential plane images.

Figure 2:
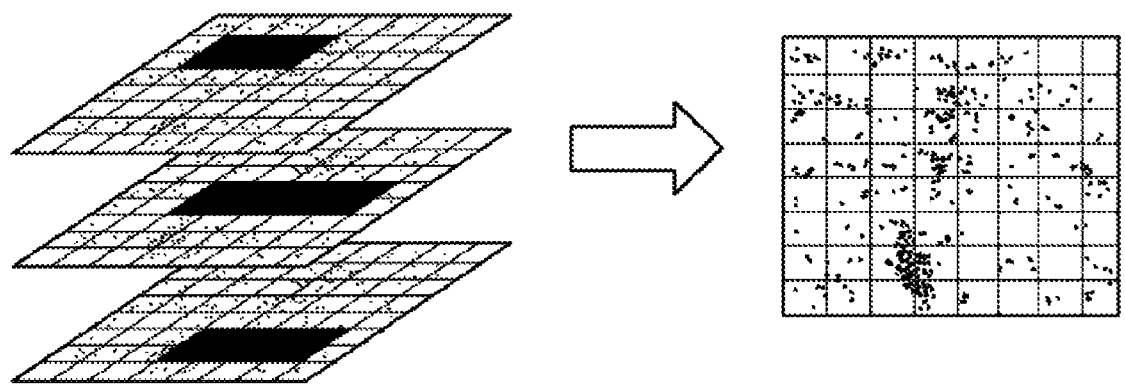
FIG. 2 is a view showing an example of forming a virtual optimal plane image.
Figure 2:
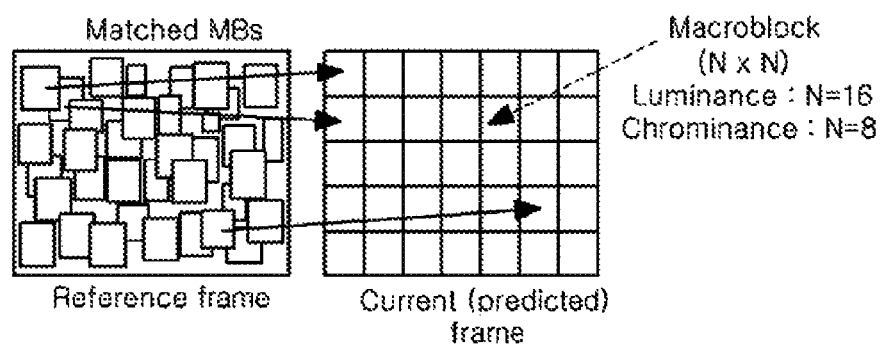

First, the optimal block selection step will be described. As described above, in order to acquire a plane image having an optimal focal point on a sample plane, the step includes acquiring a plurality of images on the basis of focal points, dividing each of the plane images into blocks, check which block has an optimal focal point for each plane, and forming one virtual plane image by combining the blocks having the optimal focal points. FIG. 2 is a view showing an example of forming a virtual optimal plane image.

Figure 3:
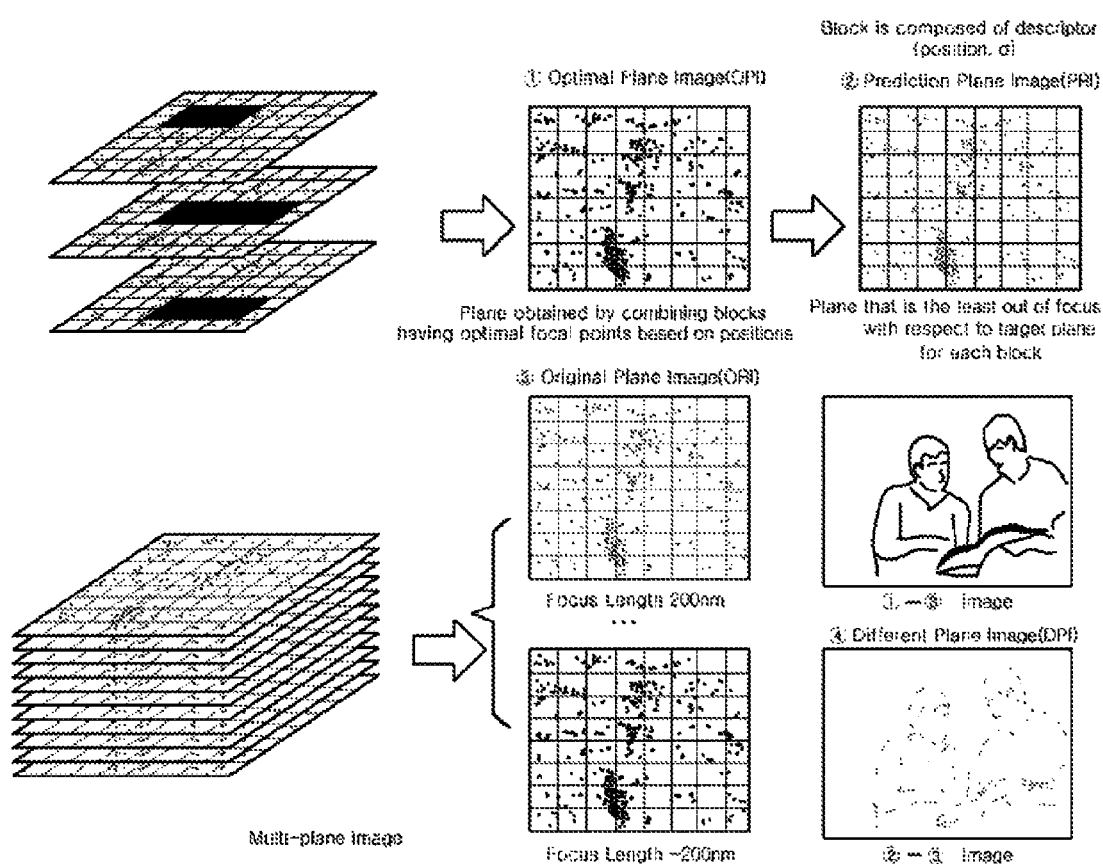
FIGS. 3 and 4 are views schematically showing the step of compressing first to nth original plane images, a virtual optimal plane image, first to nth predictive plane images, and first to nth differential plane images.
Figure 4:
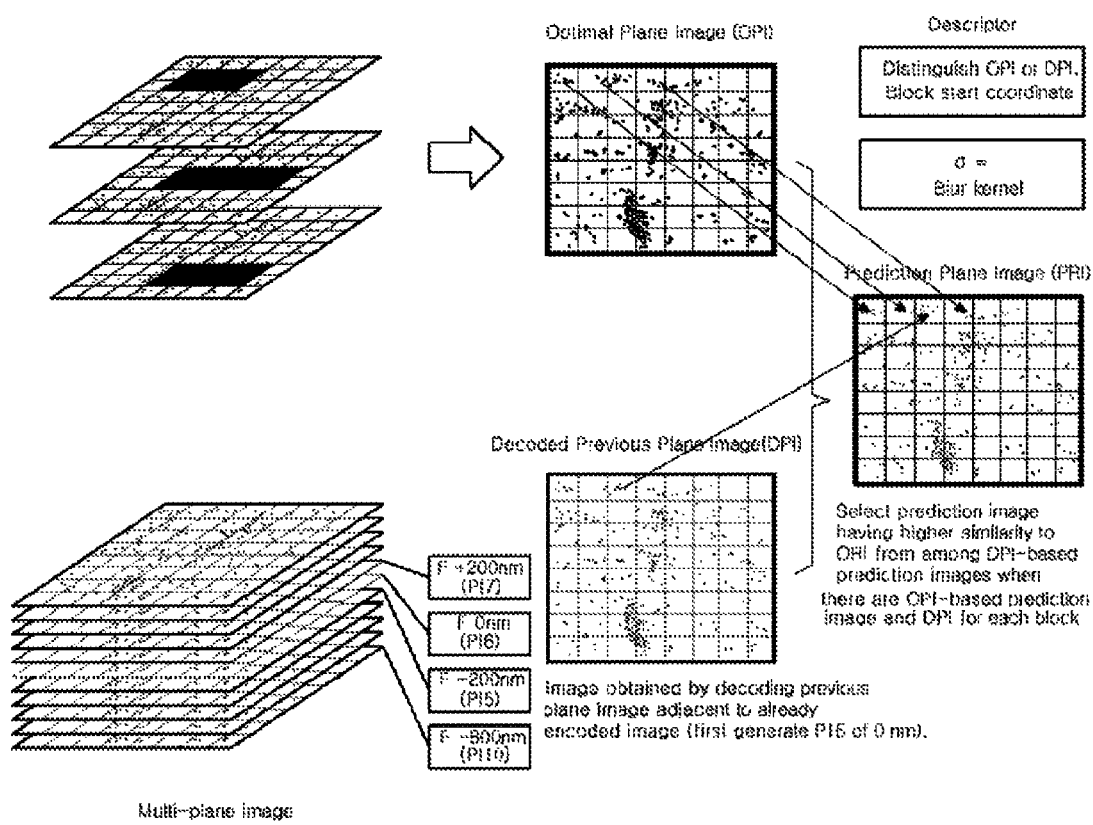

FIGS. 3 and 4 are views schematically showing the step of compressing first to nth original plane images, a virtual optimal plane image, first to nth predictive plane images, and first to nth differential plane images.

As shown in FIGS. 3 and 4, a virtual optimal plane image (OPI) is formed by combining blocks each having an optimal focal point for each position. Block descriptors for forming the first to nth original plane images are generated on the basis of the virtual OPI.

Here, each of the descriptors includes an estimated kernel for performing conversion into an original image of a corresponding plane block on the basis of location information for the block and a corresponding block of the virtual OPI.

The first to nth predictive plane images are generated from the virtual optimal plane image by using respective block descriptors, such that the first to nth predictive plane images are the least out of focus with respect to the first to nth original plane images for each block.

Then, a first differential plane image (DPI) corresponding to a difference between the first original plane image (ORI) and the first prediction plane image (PRI) and an nth DPI corresponding to a difference between the nth OR and the nth PRI are generated. As shown in FIG. 3, it can be seen that the generated differential image (②-③) has a significantly reduced amount of image data to be compressed, compared to a differential image (①-③) corresponding to a difference between the OPI and the ORI.

Last, the first to nth differential plane images are compressed.

Now, the above-described optimal block selection step will be described in more detail.

A block image quality evaluation method for a digital pathology system according to the present invention includes receiving a block to be evaluated by an image quality evaluation unit; analyzing the block to extract a foreground by the image quality evaluation unit; calculating a blur for the extracted foreground; calculating brightness distortion for the extracted foreground; calculating contrast distortion for the extracted foreground; evaluating a quality of an image of the corresponding block using the blur, the brightness distortion, and the contrast distortion by the image quality evaluation unit.

First, a foreground is extracted from the divided block.

Then, a blur for the extracted foreground is calculated. Here, in order to calculate the blur, the foreground is converted into a grey image, and a set E including all edge pixels in the foreground is found by using a sobel filter. The blur is calculated using Equation 1 below:

$$\text{Blur} = \frac{\sum_{I(x,y) \in E} \sqrt{\sum_{I(x',y') \in N_{xy}} \{I(x,y) - I(x',y')\}^2 / |N_{xy}|}}{\sum_{I(x,y) \in E} I(x,y)},$$ [Equation 1]

where $N_{xy}$ is a set of 8 pixels adjacent to a pixel $I(x, y)$, $I(x, y) \in E$, and an absolute value of $N_{xy}$ is the total number of pixels in the set $N_{xy}$.

Here, an image having good quality image denotes that the image has higher sharpness and lower blur. A shaper image has a greater change in intensity near the edge, and a more blurred image has a less change in intensity near the edge. Accordingly, the following equation for the overall image quality (IQ) of a corresponding block to be described later is set inversely proportional to the blur.

In addition, brightness distortion is calculated. For the brightness distortion, a pixel in the foreground is determined as having a brightness of 0 when the pixel is absolute black and is determined as having a brightness of 1 when the pixel is absolute white. The brightness distortion is calculated by averaging brightness values of all pixels in the foreground. A boundary value is set in consideration of a limit for a case in which the average brightness can be maximally biased. When the average brightness exceeds the boundary value, the excess is recognized as distortion. In this case, the boundary value is calculated as a statistical value in a real environment.

Here, like the blur, as the brightness distortion decreases, the image quality increases. Accordingly, the following equation for the image quality (IQ) of the final block to be described later is set such that the overall quality is set inversely proportional to the brightness distortion.

In addition, contrast distortion for the extracted foreground is calculated. In order to calculate the contrast distortion, the foreground is converted into gray, and a cumulative histogram is calculated. The contrast distortion is calculated using Equation 2 below:

Contrast distortion=(histogram binary corresponding to 75% of the maximum value of the cumulative histogram−histogram binary corresponding to 25% of the maximum value)/(maximum in range of pixel value−minimum in range of pixel value). [Equation 2]

Here, like the blur and the brightness distortion, as the contrast distortion decreases, the image quality increases.

Accordingly, the following equation for the image quality (IQ) of the final block is set such that the overall quality is set inversely proportional to the contrast distortion.

The above-described blur, brightness distortion, and contrast distortion need not be calculated in the order of description. That is, the calculations may be performed in parallel or in changed order.

Last, the overall image quality (IQ) of a corresponding block is defined as Equation 3 blow:

$$WSIQ = 1 - (ax + by + cz),$$ [Equation 3]

where $a+b+c=1$, x is a value indicating a blur, y is a value indicating brightness distortion, and z is a value indicating contrast distortion.

Here, a, b, and c are constrained by $a+b+c=1$ for normalization.

The image compression method for the digital pathology system according to the present invention may provide an optimal compression method that can effectively remove redundancy to dramatically decrease the size of a multi-plane image that conventionally had to be excessively large by using a compression algorithm according to the present invention.

While the present invention has been described with reference to a few specific embodiments, the description is illustrative of the invention and is not to be construed as limiting the invention. Various modifications may occur to those skilled in the art without departing from the spirit and scope of the invention as defined by the appended claims and their equivalents.

What is claimed is:

1. An image compression method for a digital pathology system, which is a method of compressing digital slide images having first to nth original plane images (n is a natural number greater than or equal to 2), the image compression method comprising:
   selecting a block having an optimal focal point as an optimal block from each set of blocks positioned at identical positions of the first to nth original plane images;
   forming one plane image as a virtual optimal plane image by combining only the optimal blocks;
   generating block descriptors for forming the first to nth original plane images based on the virtual optimal plane image;
   generating first to nth predictive plane images from the virtual optimal plane image such that the first to nth predictive plane images are the least out of focus by using location information for the blocks and the block descriptors;
   generating first to nth differential plane images, the first differential plane image corresponding to a difference between the first original plane image and the first predictive plane image and the nth differential plane image corresponding to a difference between the nth original plane image and the nth predictive plane image; and
   compressing the first to nth differential plane images.

2. The image compression method of claim 1, wherein each of the descriptors includes an estimated kernel for performing conversion into an original image of a corresponding plane block based on location information for the block and a corresponding block of the virtual optimal plane image.

3. The image compression method of claim 1, wherein the optimal block selection step comprises:

analyzing each of the blocks positioned at identical positions of the first to nth original plane images to extract a foreground;
calculating a blur for the extracted foreground;
calculating brightness distortion for the extracted foreground;
calculating contrast distortion for the extracted foreground; and
evaluating image quality of the corresponding block using the blur, the brightness distortion, and the contrast distortion by the image quality evaluation unit.

4. The image compression method of claim 3, wherein the calculating of a blur comprises:
finding a set E including all edge pixels in the foreground using a sobel filter; and
calculating the blur using Equation 1 below:

$$\text{Blur} = \frac{\sum_{I(x,y) \in E} \sqrt{\left| \sum_{I(x',y') \in N_{xy}} \{I(x,y) - I(x',y')\}^2 / N_{xy} \right|}}{\sum_{I(x,y) \in E} I(x,y)},$$ [Equation 1]

where $N_{xy}$ is a set of 8 pixels adjacent to a pixel $I(x, y)$, $I(x, y) \in E$, and an absolute value of $N_{xy}$ is the total number of pixels in the set $N_{xy}$.

5. The image compression method of claim 4, wherein the calculating of brightness distortion comprises:
determining that a pixel in the foreground has a brightness of 0 when the pixel is absolute black and determining that the pixel has a brightness of 1 when the pixel is absolute white; and
calculating the brightness distortion by averaging brightness values of all pixels in the foreground.

6. The image compression method of claim 5, wherein the calculating of contrast distortion comprises:
converting the foreground into gray;
calculating a cumulative histogram; and
calculating the contrast distortion using Equation 2 below:

Contrast distortion=(histogram binary corresponding to 75% of the maximum value of the cumulative histogram−histogram binary corresponding to 25% of the maximum value)/(maximum in range of pixel value−minimum in range of pixel value). [Equation 2]

7. The image compression method of claim 6, wherein the quality (IQ) of the block is defined using Equation 3 below:

$$IQ=1-(ax+by+cz),$$ [Equation 3]

where a+b+c=1, x indicates a blur, y indicates brightness distortion, and z indicates contrast distortion.

* * * * *